(12) United States Patent
Ishijima et al.

(10) Patent No.: US 7,745,782 B2
(45) Date of Patent: Jun. 29, 2010

(54) ELECTROSTATIC CHARGE MEASUREMENT METHOD, FOCUS ADJUSTMENT METHOD, AND SCANNING ELECTRON MICROSCOPE

(75) Inventors: Tatsuaki Ishijima, Tokai (JP);
Katsuhiro Sasada, Hitachinaka (JP);
Ritsuo Fukaya, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 62 days.

(21) Appl. No.: 12/038,641

(22) Filed: Feb. 27, 2008

(65) Prior Publication Data

US 2008/0203298 A1    Aug. 28, 2008

(30) Foreign Application Priority Data

Feb. 28, 2007    (JP)    ............... 2007-049927

(51) Int. Cl.
*G01N 23/00*    (2006.01)
*G21K 7/00*    (2006.01)
*H01J 37/26*    (2006.01)

(52) U.S. Cl. .............. 250/305; 250/310; 250/311; 850/10; 850/11; 850/62

(58) Field of Classification Search ......... 250/305–307, 250/310, 311, 492.1, 492.2, 492.3; 850/8, 850/10, 11, 62
See application file for complete search history.

(56) References Cited

U.S. PATENT DOCUMENTS

| | | | | |
|---|---|---|---|---|
| 4,983,830 A * | 1/1991 | Iwasaki | ............... | 850/1 |
| 6,038,018 A * | 3/2000 | Yamazaki et al. | ........ | 356/237.1 |
| 6,521,891 B1 | 2/2003 | Dotan et al. | | |
| 6,847,038 B2 * | 1/2005 | Todokoro et al. | ............... | 850/9 |
| 6,853,941 B2 * | 2/2005 | Wang et al. | ............... | 702/117 |
| 6,946,656 B2 * | 9/2005 | Ezumi et al. | ............... | 850/11 |
| 7,049,591 B2 * | 5/2006 | Todokoro et al. | ............ | 250/310 |
| 7,087,899 B2 * | 8/2006 | Ezumi et al. | ............... | 250/311 |
| 7,372,028 B2 * | 5/2008 | Ezumi et al. | ............... | 250/310 |
| 7,655,906 B2 * | 2/2010 | Cheng et al. | ............... | 250/307 |
| 2003/0016153 A1 * | 1/2003 | Wang et al. | ............... | 341/155 |
| 2004/0051041 A1 * | 3/2004 | Todokoro et al. | ............ | 250/310 |
| 2004/0211899 A1 * | 10/2004 | Ezumi et al. | ............... | 250/310 |
| 2005/0133719 A1 * | 6/2005 | Todokoro et al. | ............ | 250/310 |
| 2005/0161600 A1 * | 7/2005 | Ezumi et al. | ............... | 250/310 |
| 2006/0219918 A1 * | 10/2006 | Ezumi et al. | ............... | 250/311 |
| 2007/0040118 A1 * | 2/2007 | Cheng et al. | ............... | 250/310 |
| 2007/0221845 A1 | 9/2007 | Komuro et al. | | |
| 2008/0201091 A1 * | 8/2008 | Ezumi et al. | ............... | 702/64 |

(Continued)

FOREIGN PATENT DOCUMENTS

JP    4-229541 A    8/1992

(Continued)

*Primary Examiner*—Bernard E Souw
(74) *Attorney, Agent, or Firm*—Crowell & Moring LLP

(57) ABSTRACT

A method and a device are disclosed for suppressing error in electrostatic charge amount or defocus on the basis of electrostatic charge storage due to electron beam scanning when measuring the electrostatic charge amount of the sample or a focus adjustment amount by scanning the electron beam. An electrostatic charge measurement method, a focus adjustment method, or a scanning electron microscope for measuring an electrostatic charge amount or controlling an application voltage to the sample changes the application voltage to the energy filter while moving the scanning location of the electron beam on the sample.

10 Claims, 6 Drawing Sheets

U.S. PATENT DOCUMENTS

2008/0203298 A1 * 8/2008 Ishijima et al. ............. 250/307
2009/0057557 A1 * 3/2009 Cheng et al. ................ 250/310

FOREIGN PATENT DOCUMENTS

| JP | 2001-52642 A | 2/2001 |
| JP | 2001-236915 A | 8/2001 |
| JP | 2006-19301 A | 1/2006 |

* cited by examiner (a) Electrostatic charge distribution before scanning (b) Local surface electrostatic charge formed after scanning (c) Superimposed surface potential distribution after scanning

ELECTROSTATIC CHARGE MEASUREMENT METHOD, FOCUS ADJUSTMENT METHOD, AND SCANNING ELECTRON MICROSCOPE

BACKGROUND OF THE INVENTION

1. Field of the Invention

The present invention relates to electrostatic charge measurement methods, focus adjustment methods, and scanning electron microscopes, and in particular, an electrostatic charge measurement method, a focus adjustment method, and a scanning electron microscope for measuring or observing automatically and with a high accuracy the dimension and the shape of the pattern formed on a semiconductor wafer.

2. Description of the Related Art

The greater scale of integration and miniaturization of semiconductor devices in recent years have resulted in formation of many diverse patterns on the wafer, and evaluation and measurement of dimensions and shapes of these patterns are becoming ever more important. How fast the measurement points can be detected is critical for measuring a great number of measurement points automatically, at high speed, and with high accuracy, and for this purpose, it is necessary to focus on the pattern after shifting to the measurement point.

In order to measure the pattern dimension with high accuracy, an observing magnification is calculated from an accurate acceleration voltage in which the electrostatic charge voltage of the wafer is taken into consideration, to measure the pattern dimension. In an electron optical system, the conditions for focusing on the wafer are determined by the acceleration voltage of the electron beam and the height of the wafer.

The acceleration voltage of the electron beam is defined by an extraction voltage when the electron beam being extracted from an electron source, a retarding voltage applied to the wafer to decelerate the electron beam, and an electrostatic charge voltage of the wafer surface. A technique of controlling the application voltage to a sample according to the electrostatic charge voltage and the like of the wafer with the extraction voltage maintained constant to obtain a desired acceleration voltage regardless of the amount of electrostatic charge and the like is described in Japanese Patent Application Laid-Open No. 2001-52642, Japanese Patent Application Laid-Open No. 2001-236915 (corresponding to U.S. Pat. No. 6,521,891), and Japanese Patent Application Laid-Open No. 4-229541.

A technique of controlling the negative voltage (retarding voltage) to be applied to the sample according to the amount of electrostatic charge and the like is also referred to as a retarding focus, where the conditions for focus are changed by changing the retarding voltage while maintaining the extraction voltage of the electron beam constant, and the wafer electrostatic charge voltage of the measurement point can be calculated backwards from the retarding voltage of when focused on the wafer, the extraction voltage value, and the height of the wafer.

Japanese Patent Application Laid-Open No. 2006-19301 (corresponding to U.S. Pat. No. 6,946,656) discloses a technique of, in a scanning electron microscope equipped with an energy filter, gradually changing the application voltage to an energy filter while irradiating the sample with the electron beam, and measuring the electrostatic charge of the sample surface on the basis of the obtained graph waveform (hereinafter sometimes referred to as an S curve) indicating the transition of the detected quantity of electrons with respect to the change in application voltage to the energy filter.

SUMMARY OF THE INVENTION

In recent years, however, more and more wafers are being found to contain electrostatic charges that still remain even when the wafers are electrically grounded. The cause of such electrostatic charge is said to be due to a static electrical potential from splitting of polarized material within the resist due to friction during application of resist by a spin coater, or due to electrification from the etching process that uses plasma (such static charge will be also referred to as global electrostatic charge in the following description as it is an electrostatic charge that attaches over a wide region of the wafer (e.g., entire surface of the wafer)).

When an SOI (Silicon on Insulator) technique is used, an insulating film is formed on a wafer and a semiconductor pattern is formed on the insulating film, and thus an electrostatic charge of a few hundred volts might occur.

According to the retarding focus technique described in Japanese Patent Application Laid-Open No. 2001-52642, Japanese Patent Application Laid-Open No. 2001-236915 (corresponding to U.S. Pat. No. 6,521,891), and Japanese Patent Application Laid-Open No. 4-229541, the focus condition can be adjusted regardless of the electrostatic charge of the sample surface, but an accurate measurement sometimes cannot be performed since the sample electrostatic charge might change due to change in the retarding voltage. In particular, the amount of electrostatic charge of the global electrostatic charge or the surface potential generated at the insulating film might change with change in the retarding voltage applied to the sample. The condition for focusing on the wafer and the observing magnification of an obtained secondary electron image also change since the electrostatic charge of the wafer changes the acceleration voltage of the incoming electron beam. In this case, high speed detection of the measurement point, and high accuracy measurement of the pattern dimension cannot be performed unless the electrostatic charge voltage of the wafer under electron beam irradiation is properly measured and fed back for focusing condition and observing magnification.

The retarding focus is a technique for setting an appropriate retarding voltage based on the evaluation of sharpness and the like of the image, and thus its application is difficult unless a pattern for evaluating the sharpness is formed on the sample.

As described in Japanese Patent Application Laid-Open No. 2006-19301 (corresponding to U.S. Pat. No. 6,946,656), in the technique of measuring the amount of electrostatic charge using the S curve obtained when changing the application voltage to the energy filter, the electron beam must be scanned over a plurality of times to acquire the S curve. In particular, the global electrostatic charge is a different type of electrostatic charge from the electrostatic charge (hereinafter also referred to as localized electrostatic charge) that attaches through electron beam irradiation, where the true global electrostatic charge becomes difficult to accurately measure if electrostatic charge based on irradiation of the electron beam attaches.

It is an object of the present invention to provide a method and a device for suppressing error in amount of electrostatic charge or defocus based on the electrostatic charge storage due to electron beam scanning when measuring the amount of electrostatic charge of the sample or the focus adjustment amount by scanning the electron beam.

In order to achieve the above object, according to one aspect of the present invention, an electrostatic charge measurement method, a focus adjustment method, or a scanning electron microscope for measuring an electrostatic charge amount or controlling an application voltage to the sample by changing the application voltage to the energy filter while moving the scanning location of the electron beam on the sample is proposed.

According to such configuration, the electrostatic charge storage due to electron beam scanning can be suppressed in the process of changing the application voltage to the energy filter to measure the amount of electrostatic charge and the like.

According to such configuration, information of the electrostatic charge that was originally attached to the sample can be measured with high accuracy with minimum storage of the electrostatic charge by electron beam scanning. A high accuracy focus adjustment based on accurate electrostatic charge information can be carried out in focus adjustment.

DESCRIPTION OF THE REFERENCE NUMERALS

Figure 1:
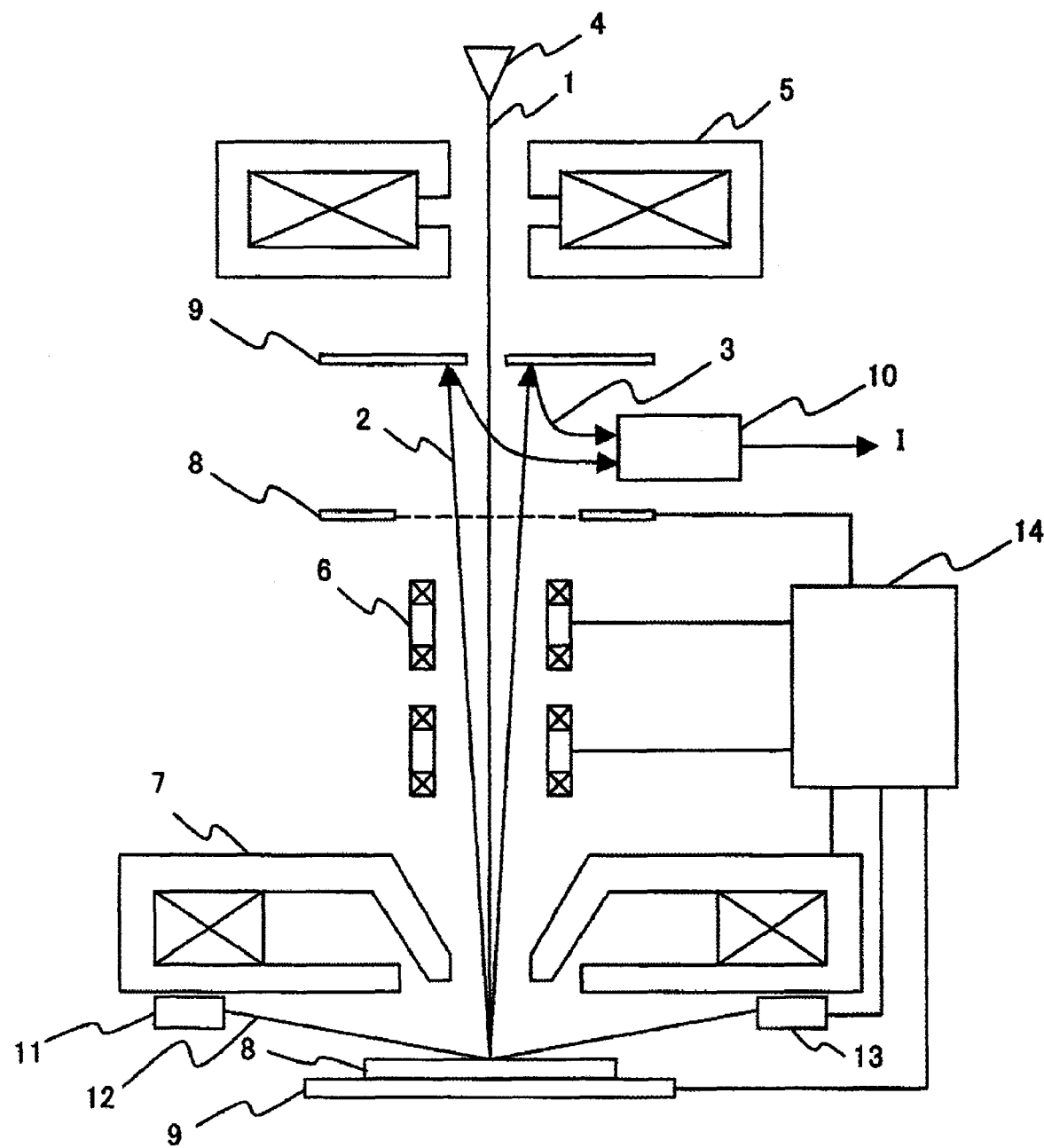
FIG. 1 is a schematic view of a scanning electron microscope.

1 Primary electron beam
2 Secondary electron
3 Secondary electron generated in conversion electrode
4 Electron source
5 Condenser lens
6 Scan deflector
7 Objective lens
8 Sample
9 Sample stage
10 Secondary electron detector
11 Laser emitter
12 Laser light
13 Position sensor
14 Control device

DESCRIPTION OF THE PREFERRED EMBODIMENTS

A scanning electron microscope described below measures the energy of the secondary electron generated from a sample when a primary electron beam is irradiated onto the sample, and calculates the electrostatic charge voltage of a region irradiated with the primary electron beam from the measurement result. The measurement of the energy is performed while applying a constant retarding voltage, similar to automatic measurement of the pattern dimension, and thus a correct electrostatic charge voltage measurement can be carried out under conditions same as the automatic measurement.

The electrostatic charges of the wafer are broadly divided into a global electrostatic charge voltage $\Delta Vg$ and a localized electrostatic charge voltage $\Delta Vs$. The global electrostatic charge voltage $\Delta Vg$ refers to the electrostatic charge of a wide region that influences both focus and magnification, whereas the localized electrostatic charge voltage $\Delta Vs$ refers to the electrostatic charge of a narrow region that influences only magnification such as electrostatic charge that accumulates when irradiation of the primary electron beam onto the same region of the sample is continued. Although only $\Delta Vg$ needs to be correctly measured for focusing, an invention for suppressing $\Delta Vs$ to zero as much as possible is simultaneously required since the sum of $\Delta Vg$ and $\Delta Vs$ is calculated from the energy of the secondary electron.

The secondary electron is constantly generated regardless of the presence of the pattern, and thus automatic detection of the pattern does not need to be performed beforehand as in the retarding focus system, and the wafer electrostatic charge voltage can be measured at high speed.

The embodiment of the present invention will be described using the drawings.

FIG. 1 shows a schematic view of a scanning electron microscope. The primary electron 1 (electron beam) extracted from the electron source is narrowed by a condenser lens 5, and then two-dimensionally scanned on a wafer by a scan deflector 6. The primary electron is decelerated by a retarding voltage Vr applied to a sample 8 by way of a sample stage 9, converged by the lens effect of an objective lens 7, and irradiated onto the wafer.

When the primary electron 1 is irradiated onto the wafer, a secondary electron 2 is generated, and is accelerated in the electron source direction by the retarding voltage Vr. When the secondary electron 2 hits a conversion electrode 9, a secondary electron 3 newly generated from the conversion electrode 9 is trapped by a secondary electron detector 10, whereby the output I of the secondary electron detector changes according to the quantity of the secondary electron 3. The luminance adjustment of a display is carried out according to the output I. An example of once converting the secondary electron emitted from the sample with the conversion electrode and then detecting the resultant has been described in the description of FIG. 1, but the configuration is obviously not limited thereto, and a configuration of arranging an electron multiplier tube or a detection surface of the detector on a trajectory of the accelerated secondary electron or a backscattered electron may be adopted.

A control device 14 has a configuration capable of controlling the negative voltage (retarding voltage) to be applied to the sample and the voltage to be applied to a mesh electrode 8 of an energy filter. The control device 14 incorporates a storage medium (not shown) for storing programs to automatically perform the control described below.

In the present example, the energy filter of the secondary electron is provided as a means for measuring the global electrostatic charge voltage $\Delta Vg$. For example, the mesh electrode 8 is arranged under the conversion electrode 9 to sweep the application voltage Ve of the mesh electrode 8, with the retarding voltage Vr applied when there are no electrostatic charges at the wafer as a base point, and to measure the change in signal quantity of the secondary electron (so-called S curve).

Figure 2:
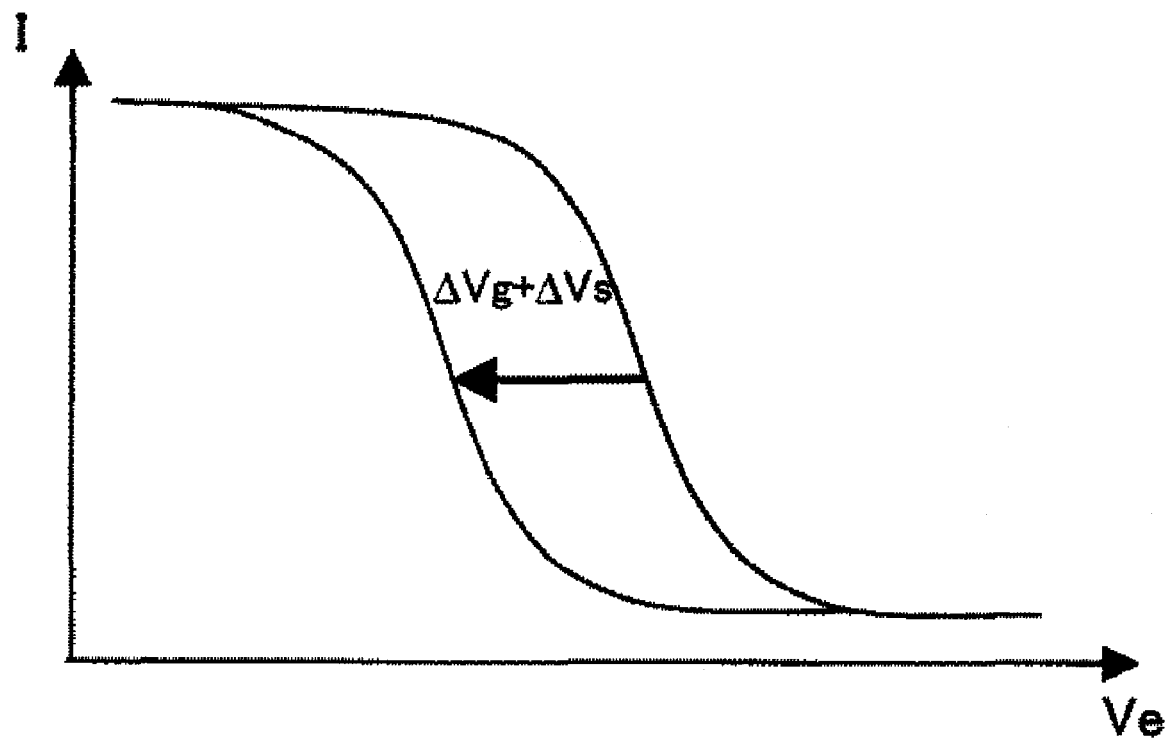
FIG. 2 is a graph showing transition of an output I of a secondary electron detector with respect to change in application voltage Ve to an energy filter.

FIG. 2 shows an example of a measured S curve. The horizontal axis is the application voltage Ve to the mesh electrode 8, and the vertical axis is the electron detection amount I. The sum of the global electrostatic charge voltage $\Delta Vg$ and the localized electrostatic charge voltage $\Delta Vs$ is obtained from the shift voltage by comparing the S curve measured at the sample having a conductive surface and the S curve at the observation point of the actual sample. Normally, the global electrostatic charge voltage $\Delta Vg$ refers to the electrostatic charges distributed over a wide range of greater than or equal to about 2.7 mm square in FOV on the sample at a magnification of about 50 k times. The localized electrostatic charge voltage ΔVs refers to the electrostatic charges of a narrow range of smaller than or equal to about 0.27 mm square in FOV on the sample at a magnification of greater than or equal to about 500 times. 50 to 500 times can be the transition magnification from the localized electrostatic charge to the global electrostatic charge. If the global electrostatic charge voltage is correctly measured, auto focus can be achieved by combining it with a sensor for measuring the physical height of the sample. The sensor for measuring the sample height includes a light source 11 and a light receiving part 13, and is configured to measure the height of the sample according to the reflection position of a laser light 12 emitted from the light source 11.

A sample whose surface has a composition same as that of the sample to be actually measured and which is not attached with global electrostatic charge can be collected for a standard sample for creating the S curve that serves as a reference. As described above, global electrostatic charge is accumulated during the semiconductor manufacturing process, where if a sample having the same sample surface configuration is found without going through such process, such sample can be used as a standard sample for creating the reference S curve.

Figure 3:
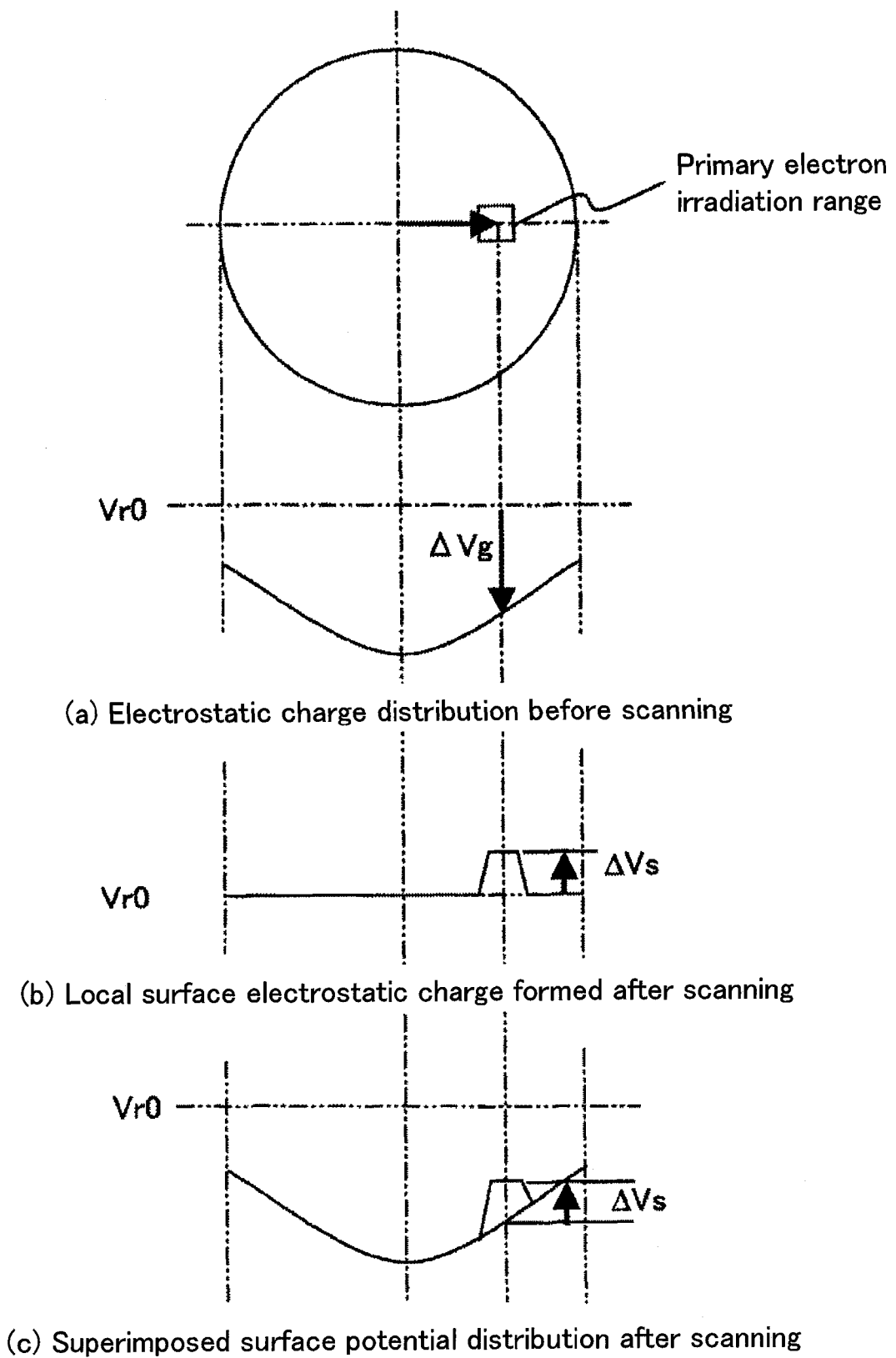
FIG. 3 is a view describing change in electrostatic charge of before and after electron beam scanning.

FIG. 3 shows change in the sample electrostatic charge voltage of before and after scanning. Since the localized electrostatic charge voltage ΔVs generates when scanning of the same region on the wafer is repeated, ΔVs can be assumed as substantially zero by using the region that has not been scanned for the measurement of the S curve. Therefore, measurement of only the global electrostatic charge voltage ΔVg by use of the energy filter can be carried out.

Figure 4:
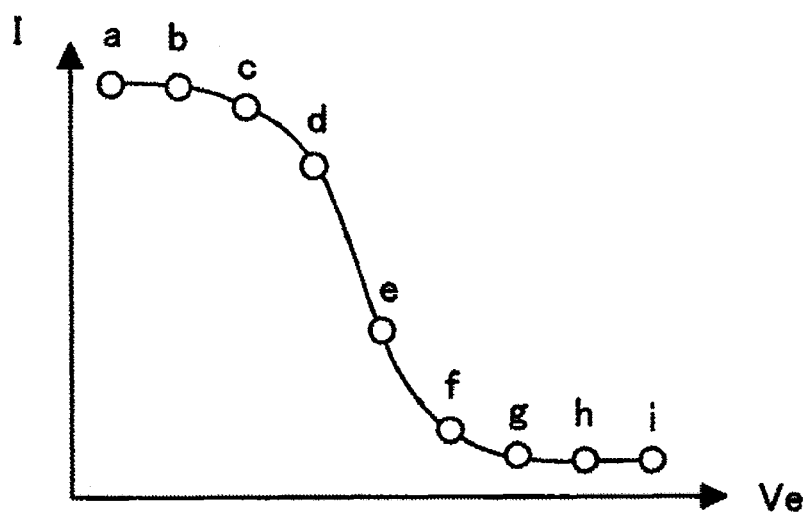
FIG. 4 is a view describing a scanning method for measuring global electrostatic charge while suppressing localized electrostatic charge.
Figure 4:
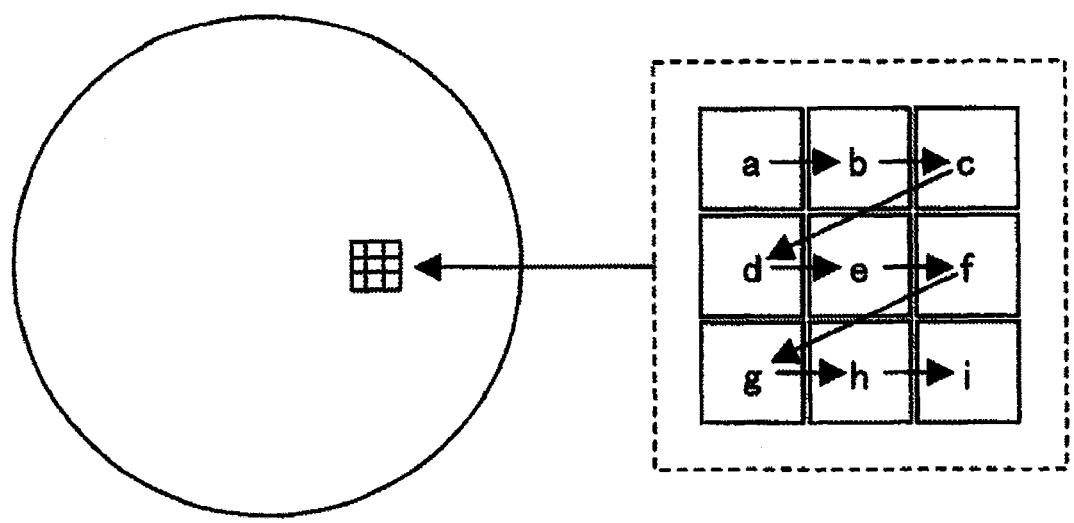

FIG. 4 shows a method of drawing the S curve without actually increasing ΔVs. A region of about 27 to 270 micron square at which the localized electrostatic charge voltage ΔVs is stable and the global electrostatic charge voltage ΔVg is not influenced at the periphery of the location to be measured is finely divided by the number of measurement points necessary for plotting the S curve. If measurement of a total of nine points is necessary for plotting the S curve, the region per one measurement may be 9 to 90 micron square, or the region may be equally divided laterally into nine areas.

Figure 5:
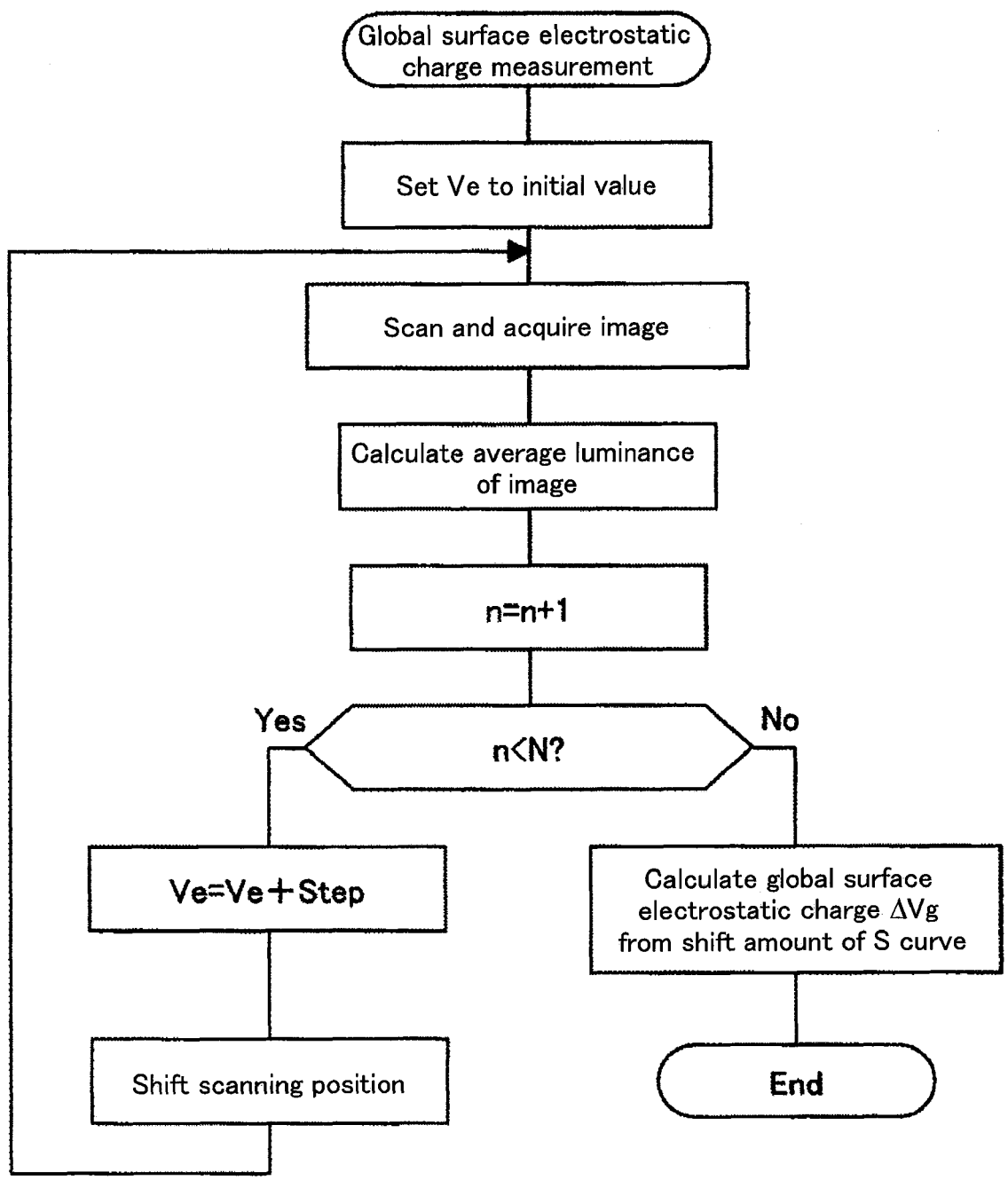
FIG. 5 is a flowchart showing a process of measuring global electrostatic charge.

As shown in the procedure of the global surface electrostatic charge measurement of FIG. 5, the application magnification to the energy filter and the scanning region used for one measurement are simultaneously shifted to calculate the average luminance of the image under each condition. Since the average luminance can be calculated even if a pattern does not exist in the region to be used, coarse adjustment of the focus can be performed at higher speed than the auto focus that involves pattern detection and image processing as in the prior art. The measurement is stopped when the average luminance becomes lower than or equal to a given threshold value and the shift voltage is immediately calculated, so that higher speed can be further achieved.

In the example of FIG. 4, the scanning position for electrostatic charge measurement is arrayed in a matrix form, but is not limited thereto, and the scanning position can be arrayed one-dimensionally. In particular, the global electrostatic charge is an electrostatic charge having a potential that is a maximum at the center of the sample and gradually decreases towards the edge of the sample. That is, in the case of a circular wafer, the electrostatic charges are distributed concentrically. In order to measure the electrostatic charges with high accuracy, the scanning position for electrostatic charge measurement is desirably arrayed in the circumferential direction of the wafer. In particular, the scanning position is desirably arrayed along the radial position same as the actual measurement length and inspection position or a perpendicular line with respect to a line extending in the radial direction of the wafer.

The position at which the global electrostatic charge indicates substantially the same value can be selectively set as a scanning position for electrostatic charge measurement by arraying the scanning positions in such a manner. The scanning position can be arrayed in the radial direction of the wafer in a matrix form obviously within the allowable margin of error.

The amount of electrostatic charge (ΔVg+ΔVs) can be measured by comparing the S curve obtained as above that serves as a reference with the S curve obtained from the measurement target sample. According to the above example, an extremely accurate ΔVg can be obtained since increase in ΔVs can be minimized. A specific method of calculating ΔVg includes obtaining the potential difference between two peaks obtained by differentiating the reference S curve and the S curve obtained from the measurement target sample.

According to such calculation, the potential difference can be accurately identified even if a large difference is created in the secondary electron detection amount between the two S curves. The ΔVg can be measured other than through such calculation method by calculating the difference between the mesh voltages from which the specific electron detection amount is obtained. In this example, ΔVg is assumed as the global electrostatic charge amount of the electrostatic charge measurement site, but if some other variable elements exist, the addition result of the predetermined amount ΔVc thereof and ΔVg can also be assumed as the amount of electrostatic charge if the values of the variable elements are identified in advance.

ΔVg or ΔVg+ΔVc can be applied to the retarding voltage as focus amount for retarding focus. Focus adjustment can be performed by converting the focus corresponding to ΔVg into the excitation current to the objective lens 7 and changing the excitation current. For this purpose, the control device 14 may store the relationship between ΔVg and the excitation current Iobj in a table form in advance, so that the excitation current is obtained on the basis of the calculated ΔVg.

Figure 6:
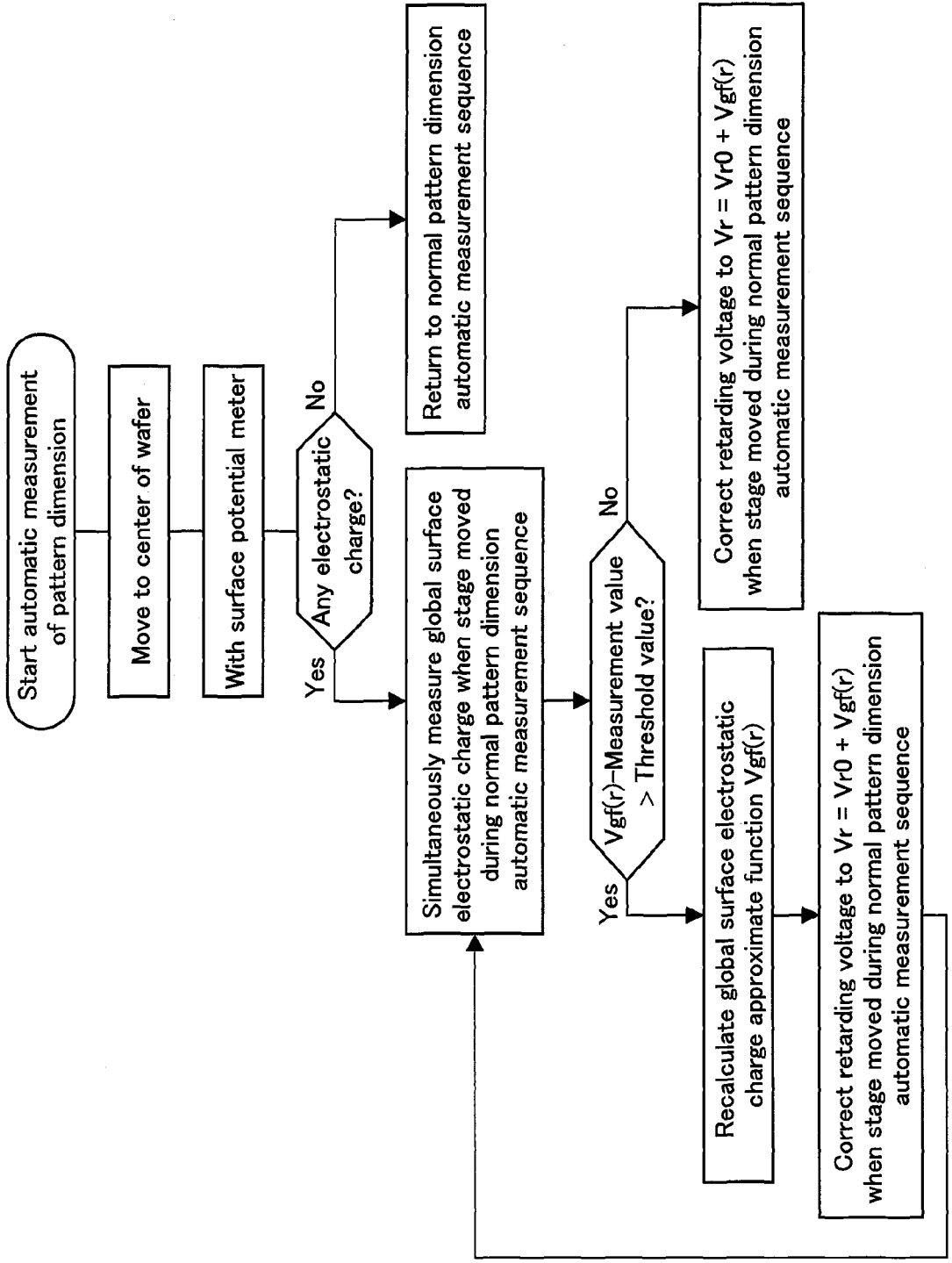
FIG. 6 is a flowchart showing a process of automatically measuring a sample having a possibility of being electrostatically charged.

FIG. 6 shows a method of measuring the global surface electrostatic charge during the execution of an automatic measurement sequence of a pattern dimension, and correcting the focus and the magnification by changing the retarding voltage Vr. Normally, the center of the wafer is electrostatically charged the most, and thus the global surface electrostatic charge is measured at the central part of the wafer, and determination is made as no electrostatic charge if it falls within a range of a certain threshold value, whereby the process returns to the normal sequence. Determination is made as electrostatic charge present if exceeding the threshold value, and the measurement is repeated until an optimum global surface electrostatic charge approximate function Vgf (r) is obtained. The global surface electrostatic charge approximate function Vgf(r) refers to approximating the surface potential distribution of the wafer from N measurement results by a high-order even function of $Vg(r)=k_1 \cdot r^{2(N-1)}+k_2 \cdot r^{2(N-2)}+ \ldots +k_{N-1} \cdot r^2+k_N$ on the assumption that the global surface electrostatic charge is constant according to the distance r from the center of the wafer. The order and the accuracy of the approximate function increase with increase in measurement results.

The measurement of the global surface electrostatic charge is performed only when the stage is moved during the execution of the automatic measurement sequence of the pattern dimension. The influence on the throughput of the automatic measurement sequence of the pattern dimension can be suppressed by suppressing the stage movement for only the measurement of the global surface electrostatic charge. The local surface electrostatic charge is prevented from causing error in pattern dimension measurement by performing the measurement of the global surface electrostatic charge at a region that does not overlap the region used for the actual pattern dimension measurement by using the scan deflector.

When a difference between the global surface electrostatic charge approximate function Vgf(r) and the actual measurement value falls within a given threshold value, sufficient accuracy of the approximate function is assumed to have been obtained, and subsequent measurements are not performed. Until the final approximate function is obtained, the approximate electrostatic charge voltage of the next measurement point can be estimated from the equation in the middle, and thus optimization of the range of the voltage applied to the energy filter can be performed in a form of feeding back to the retarding voltage Vr in the next measurement. Thus, the reliability is enhanced and higher speed of the measurement itself is further achieved.

According to one aspect of the present invention, the global electrostatic charge can be accurately measured without changing the retarding voltage while applying the retarding voltage. Since change in retarding voltage induces change in amount of electrostatic charge, the method of the present example to measure the amount of electrostatic charge without changing the retarding voltage is very effective.

When measuring the potential of the sample surface by use of the energy filter, the application voltage to the energy filter is changed and the change in secondary electron quantity at the time must be reviewed, and thus the electron beam needed to be continuously irradiated during the relevant time, but according to one aspect of the present invention, the change in secondary electron quantity is detected by irradiating the electron beam to different scanning sites, and the measurement error of the global electrostatic charge due to localized electrostatic charge storage can be reduced.

What is claimed is:

1. An electrostatic charge measurement method for measuring electrostatic charge of a sample on the basis of secondary electron emission detection, comprising:
    scanning a primary electron beam on said sample whereby the sample surface becomes electrostatically charged;
    arranging an energy filter relative to said sample for energy filtering the secondary electron emission from said sample;
    acquiring a reference curve based on another sample without a global electrostatic charge;
    applying different voltages to said energy filter for every electron beam irradiation while shifting the beam to a different location on said sample to obtain a curve indicating change in quantity of said detected secondary electron emission with respect to change in application voltage to said energy filter; and
    comparing the obtained curve and the reference curve to measure electrostatic charge amount of the sample from which said first curve is acquired.

2. The electrostatic charge measurement method according to claim 1, wherein said reference curve is acquired by an electron beam irradiation on a sample in which an irradiation region of said electron beam is conductive.

3. A scanning electron microscope comprising an electron source, a scan deflector for scanning an electron beam emitted from the electron source on a sample, a detector for detecting secondary electron emission obtained based on the electron beam scanning on the sample; an energy filter for performing energy filtering on the secondary electron emission from said sample; and a control device for controlling an application, voltage to the energy filter; wherein
    said control device is configured to apply different voltages to said energy filter for every electron beam irradiation while shifting the beam to a different location with respect said sample to detect change in quantity of said detected secondary electron emission with respect to change in the application voltage to said energy filter, and to calculate an electrostatic charge amount of said sample or the application voltage applied to said sample based on said application voltage where a predetermined detection electron quantity has been obtained.

4. The scanning electron microscope according to claim 3, wherein said control device controls the application voltage to said sample to perform an electron beam irradiation to different locations with respect to said sample with a voltage to be applied to said sample being kept constant.

5. The scanning electron microscope according to claim 3, wherein said control device calculates the electrostatic charge amount of said sample or the application voltage applied to said sample based on a difference between said application voltage and a voltage value stored in advance.

6. The scanning electron microscope according to claim 3, wherein said control device stops electron detection, and calculates said electrostatic charge amount or the application voltage applied to the sample when said detection amount is lower than or equal to a predetermined threshold value.

7. The scanning electron microscope according to claim 3, wherein said control device is arranged to perform the electrostatic charge measurement at a center of said sample, and stops the electroststatic charge measurement when the electrostatic charge voltage is less than or equal to a predetermined threshold value, and continues the electrostatic charge measurement when exceeding the predetermined threshold value.

8. The scanning electron microscope according to claim 3, wherein said control device obtains a distribution of the electrostatic charge as a function with respect to a distance in said sample surface direction on the basis of a result of the electrostatic charge measurement of a plurality of regions on the sample, and calculates an electrostatic charge voltage of an arbitrary location on said sample based on the function.

9. The scanning electron microscope according to claim 8, wherein said control device calculates a voltage to be applied to said sample based on said function.

10. A method of adjusting a focus of an electron beam on the basis of detected secondary electron comprising:
    scanning an electron beam on a sample whose surface becomes electrostatically charged;
    arranging an energy filter for energy filtering secondary electron emission from said sample;
    acquiring a reference curve based on another sample whose surface is free of an electrostatic charge;
    applying different voltages to said energy filter for every electron beam irradiation while shifting the beam to a different location on said sample to form a curve indicating a change in quantity of said detected secondary electron emission with respect to change in application voltage to said energy filter; and
    the formed curve and the acquired curve are compared to calculate a negative voltage to be applied to said sample.

* * * * *